United States Patent [19]
McCormack et al.

[11] Patent Number: 5,964,742
[45] Date of Patent: Oct. 12, 1999

[54] NONWOVEN BONDING PATTERNS PRODUCING FABRICS WITH IMPROVED STRENGTH AND ABRASION RESISTANCE

[75] Inventors: Ann Louise McCormack, Cumming, Ga.; David Lee Fuqua, Huntsville, Ala.; Kevin Edward Smith, Knoxville, Tenn.

[73] Assignee: Kimberly-Clark Worldwide, Inc., Neenah, Wis.

[21] Appl. No.: 08/929,808

[22] Filed: Sep. 15, 1997

[51] Int. Cl.$^6$ ........................................... A61F 13/15
[52] U.S. Cl. ........................... 604/380; 604/358; 428/198
[58] Field of Search ................................. 604/358, 380; 428/198

[56] References Cited

U.S. PATENT DOCUMENTS

| | | |
|---|---|---|
| D. 7,178 | 2/1874 | Campbell . |
| D. 43,596 | 2/1913 | Foster . |
| D. 81,838 | 8/1930 | Maurus . |
| D. 99,990 | 6/1936 | Brezner . |
| D. 101,310 | 9/1936 | Lehmann . |
| D. 102,691 | 1/1937 | Levy . |
| D. 104,266 | 4/1937 | Jaeger . |
| D. 154,162 | 6/1949 | Ryan . |
| D. 188,408 | 7/1960 | Siegmann . |
| D. 298,701 | 11/1988 | Drew . |
| D. 298,702 | 11/1988 | Drew . |
| 3,338,992 | 8/1967 | Kinney . |
| 3,341,394 | 9/1967 | Kinney . |
| 3,502,763 | 3/1970 | Hartmann . |
| 3,542,615 | 11/1970 | Dobo et al. . |
| 3,692,618 | 9/1972 | Dorschner et al. . |
| 3,802,817 | 4/1974 | Matsuki et al. . |
| 3,849,241 | 11/1974 | Butin et al. . |
| 3,855,046 | 12/1974 | Hansen et al. . |
| 3,949,127 | 4/1976 | Ostermeier et al. . |
| 4,048,364 | 9/1977 | Harding et al. . |
| 4,100,324 | 7/1978 | Anderson et al. . |
| 4,135,021 | 1/1979 | Patchell et al. . |
| 4,154,885 | 5/1979 | Tecl et al. . |
| 4,187,343 | 2/1980 | Akiyama et al. . |
| 4,188,436 | 2/1980 | Ellis et al. . |
| 4,265,954 | 5/1981 | Romanek . |
| 4,276,336 | 6/1981 | Sabee . |
| 4,340,563 | 7/1982 | Appel et al. . |
| 4,443,513 | 4/1984 | Meitner et al. . |
| 4,472,328 | 9/1984 | Sugimoto et al. . |
| 4,493,868 | 1/1985 | Meitner . |
| 4,573,991 | 3/1986 | Pieniak et al. . |
| 4,588,630 | 5/1986 | Shimalla . |
| 4,699,733 | 10/1987 | Matsumura et al. . |
| 4,778,460 | 10/1988 | Braun et al. . |
| 4,818,464 | 4/1989 | Lau . |

(List continued on next page.)

FOREIGN PATENT DOCUMENTS

| | | |
|---|---|---|
| 97/11661 | 4/1997 | WIPO . |
| 97/11662 | 4/1997 | WIPO . |
| 97/24482 | 7/1997 | WIPO . |

OTHER PUBLICATIONS

S. N. 08/754,519 filed Dec. 17, 1997, "Pattern–Unbonded Nonwoven Web and Process for Making the Same".
S. N. 08/929,432 filed Sep. 15, 1997, "Breathable Barrier Composite Useful as an Ideal Loop Fastener Component".
S. N. 08/929,561 filed Sep. 15, 1997, "Stretch–Pillowed Bulked Laminate Useful as an Ideal Loop Fastener Component".

*Primary Examiner*—John G. Weiss
*Assistant Examiner*—Dennis Ruhl
*Attorney, Agent, or Firm*—James B. Robinson

[57] ABSTRACT

There is disclosed a thermal bonding pattern for nonwoven fabric comprising a pattern having an element aspect ratio between about 2 and about 20 and an unbonded fiber aspect ratio of between about 3 and about 10. It has been unexpectedly found that such a fabric has a higher abrasion resistance and strength than a similar fabric bonded with different bond patterns of similar bond areas. This combination of strength and abrasion resistance has long been sought after.

21 Claims, 3 Drawing Sheets

U.S. PATENT DOCUMENTS

| | | |
|---|---|---|
| 4,867,150 | 9/1989 | Gilbert . |
| 4,908,251 | 3/1990 | Iimura et al. . |
| 4,965,122 | 10/1990 | Morman . |
| 4,981,747 | 1/1991 | Morman . |
| 5,108,827 | 4/1992 | Gessner . |
| 5,114,781 | 5/1992 | Morman . |
| 5,244,482 | 9/1993 | Hassenboehler, Jr. . |
| 5,277,976 | 1/1994 | Hogle et al. . |
| 5,296,289 | 3/1994 | Collins . |
| 5,382,400 | 1/1995 | Pike et al. . |
| 5,620,779 | 4/1997 | Levy et al. . |
| 5,626,571 | 5/1997 | Young et al. . |
| 5,628,097 | 5/1997 | Benson et al. . |

NONWOVEN BONDING PATTERNS PRODUCING FABRICS WITH IMPROVED STRENGTH AND ABRASION RESISTANCE

FIELD OF THE INVENTION

The present invention relates to the field of nonwoven fabrics like those produced by the meltblowing and spunbonding processes. Such fabrics are used in a myriad of different products such as garments, personal care products, infection control products, outdoor fabrics and protective covers.

BACKGROUND OF THE INVENTION

Nonwoven fabrics produced by the meltblowing and spunbonding process have found great utility in many diverse applications from car and boat covers to incontinence products. Different attributes or properties of the fabric are required depending on the application. A car cover, for example, must have great tensile strength and resistance to ultraviolet radiation, while a feminine hygiene product must exhibit great absorbency and softness. Developing just the right combination of properties for the application is a complex task requiring the focused attention of many highly qualified individuals.

The bonding pattern used in either bonding the fibers of the nonwoven fabric to itself or in bonding the nonwoven fabric to other material layers can cause great changes in the fabric properties. Bonding patterns with large bond areas, for example, tend to make a strongly bonded but rough feeling fabric. Those with small bond areas tend to make soft feeling but very weak fabric.

Various attempts have been made at overcoming the disadvantage seemingly inherent in higher bond areas, i.e. decreased softness. One such attempt is taught in U.S. Pat. No. 5,620,779 to Levy and Mcormack and is a nonwoven fabric with a bond pattern having a certain required spacing ratio which is then stretched to produce ribs.

A number of treatments have also been developed to soften nonwoven fabrics such as multiple washings and chemical treatments.

There remains a need, however, for an unribbed fabric without chemical treatments having good bonding strength (i.e. tensile strength and abrasion resistance) yet also having good fabric softness without excessive bonding area.

Accordingly, it is an object of this invention to provide a nonwoven fabric with a bonding area comparable to fabrics bonded with known patterns yet having greater softness and comparable or better tensile strength and abrasion resistance.

SUMMARY OF THE INVENTION

The objects of the invention are met by a thermal bonding pattern for nonwoven fabric comprising a pattern having an element aspect ratio between about 2 and about 20 and an unbonded fiber aspect ratio of between about 3 and about 10. It has been unexpectedly found that such a fabric has a higher abrasion resistance and strength than a similar fabric bonded with different bond patterns. In alternative embodiments, the fabric may be perforated or apertured by stretching after bonding according to known techniques.

DEFINITIONS

Figure 1:
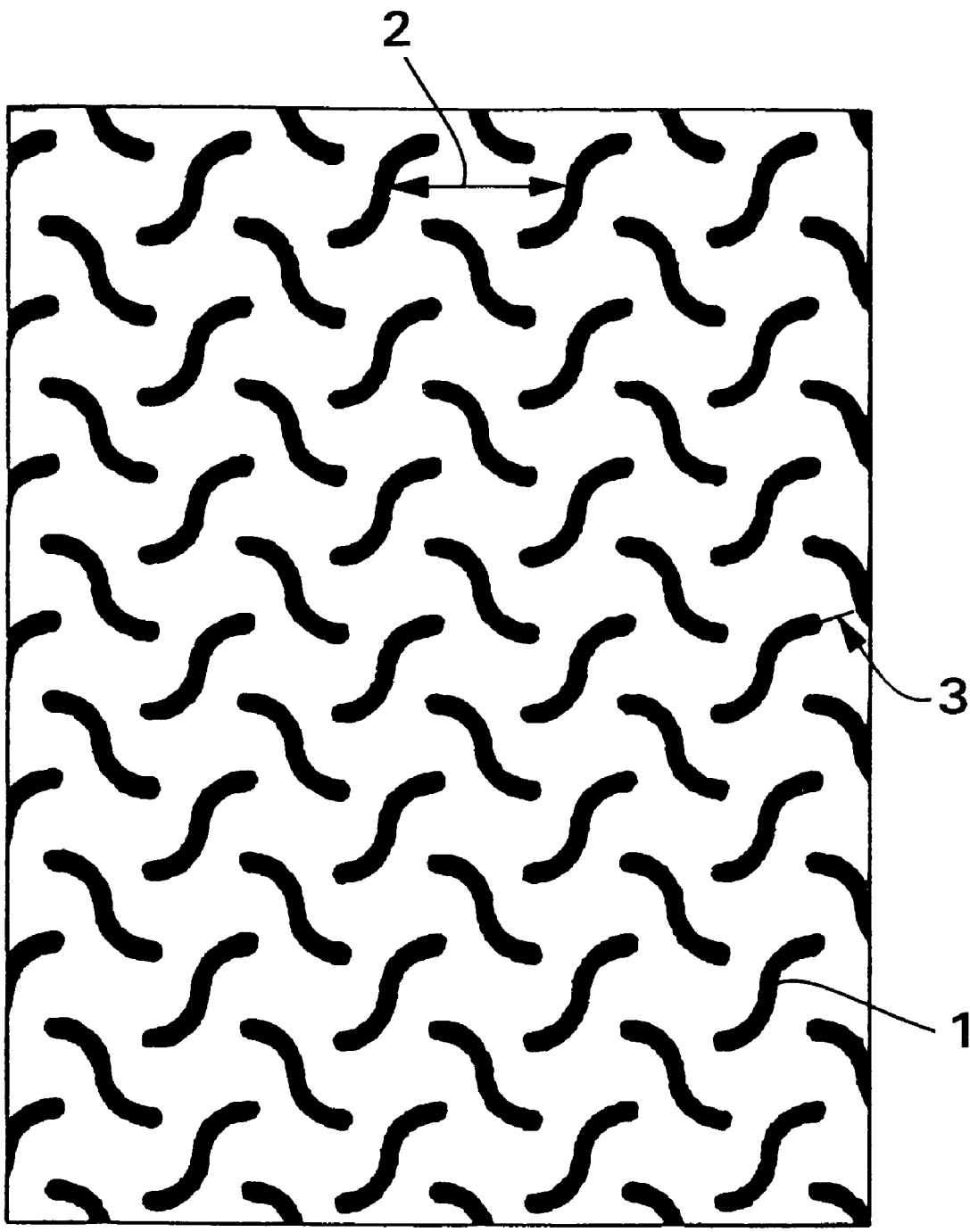
FIG. 1 is a drawing of a bonding pattern satisfying the requirements of this invention and called the S-weave pattern.

"Hydrophilic" describes fibers or the surfaces of fibers which are wetted by the aqueous liquids in contact with the fibers. The degree of wetting of the materials can, in turn, be described in terms of the contacts angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than 90° are designated "nonwettable" or hydrophobic.

"Layer" when used in the singular can have the dual meaning of a single element or a plurality of elements.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "text", which is defined as the grams per kilometer of fiber. Tex may be calculated as denier/9.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be wood pulp, superabsorbent particles, cellulose or staple fibers, for example. Coform processes are shown in commonly assigned U.S. Pat. No. 4,818,464 to Lau and U.S. Pat. No. 4,100,324 to Anderson et al. Webs produced by the coform process are generally referred to as coform materials.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught, for example, in U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. No. 5,277,976 to Hogle et al. which describes fibers with unconventional shapes. "Biconstituent fibers" refers to fibers which have been formed from at least two polymers extruded from the same extruder as a blend. The term "blend" is defined below. Biconsfituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen-Pennings or "H&P" pattern with about a 30% bond area with about 200 pins/square inch as taught in U.S. Pat. No. 3,855,046 to Hansen and Pennings. The H&P pattern has square point or pin bonding areas. Another typical point bonding pattern is the expanded Hansen-Pennings or "EHP" bond pattern which produces a 15% bond area. Another typical point bonding pattern designated "714" has square pin bonding areas wherein the resulting pattern has a bonded area of about 15%. Other common patterns include a diamond pattern with repeating and slightly offset diamonds with about a 16% bond area and a wire weave pattern looking as the name suggests, e.g. like a window screen, with about an 18% bond area. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

As used herein "pattern unbonded" or interchangeably "point unbonded" or "PUB", means a fabric pattern having continuous thermally bonded areas defining a plurality of discrete unbonded areas. The fibers or filaments within the discrete unbonded areas are dimensionally stabilized by the continuous bonded areas that encircle or surround each unbonded area, such that no support or backing layer of film or adhesive is required. The unbonded areas are specifically designed to afford spaces between fibers or filaments within the unbonded areas. A suitable process for forming the pattern-unbonded nonwoven material of this invention includes providing a nonwoven fabric or web, providing opposedly positioned first and second calender rolls and defining a nip therebetween, with at least one of said rolls being heated and having a bonding pattern on its outermost surface comprising a continuous pattern of land areas defining a plurality of discrete openings, apertures or holes, and passing the nonwoven fabric or web within the nip formed by said rolls. Each of the openings in said roll or rolls defined by the continuous land areas forms a discrete unbonded area in at least one surface of the nonwoven fabric or web in which the fibers or filaments of the web are substantially or completely unbonded. Stated alternatively, the continuous pattern of land areas in said roll or rolls forms a continuous pattern of bonded areas that define a plurality of discrete unbonded areas on at least one surface of said nonwoven fabric or web. Alternative embodiments of the aforesaid process includes pre-bonding the nonwoven fabric or web before passing the fabric or web within the nip formed by the calender rolls, or providing multiple nonwoven webs to form a pattern-unbonded laminate. The point unbonded pattern and process are described in U.S. Pat. application Ser. No. 08/754,419 and an example may be seen in FIG. 4.

As used herein, the term "element aspect ratio" refers to the ratio between the length of an element or pin in a bonding pattern to the width of the same element, calculated as length of an element measured along its centerline divided by width of the element.

As used herein, the term "unbonded fiber aspect ratio" refers to the ratio between the longest and shortest distances between elements or pins of a bond pattern within a repeating pattern. This ratio is calculated as the longest distance divided by the shortest distance.

As used herein, the terms "necking" or "neck stretching" interchangeably refer to a method of elongating a nonwoven fabric, generally in the machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions. Such a process is disclosed, for example, in U.S. Pat. No. 4,443,513 to Meitner and Notheis, U.S. Pat. Nos. 4,965,122, 4,981,747 and 5,114,781 to Morman and U.S. Pat. No. 5,244,482 to Hassenboehler Jr. et al.

As used herein, the term "garment" means any type of non-medically oriented apparel which may be worn. This includes industrial work wear and coveralls, undergarments, pants, shirts, jackets, gloves, socks, and the like.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

As used herein, the term "personal care product" means diapers, training pants, absorbent underpants, adult incontinence products, and feminine hygiene products.

As used herein, the term "protective cover" means a cover for vehicles such as cars, trucks, boats, airplanes, motorcycles, bicycles, golf carts, etc., covers for equipment often left outdoors like grills, yard and garden equipment (mowers, roto-tillers, etc.) and lawn furniture, as well as floor coverings, table cloths and picnic area covers.

As used herein, the term "outdoor fabric" means a fabric which is primarily, though not exclusively, used outdoors. Outdoor fabric includes fabric used in protective covers, camper/trailer fabric, tarpaulins, awnings, canopies, tents, agricultural fabrics and outdoor apparel such as head coverings, industrial work wear and coveralls, pants, shirts, jackets, gloves, socks, shoe coverings, and the like.

Test Methods

Grab Tensile test: The grab tensile test is a measure of breaking strength and elongation or strain of a fabric when subjected to unidirectional stress. This test is known in the art and conforms to the specifications of Method 5100 of the Federal Test Methods Standard 191A. The results are expressed in pounds or grams to break and percent stretch before breakage. Higher numbers indicate a stronger, more stretchable fabric. The term "load" means the maximum load or force, expressed in units of weight, required to break or rupture the specimen in a tensile test. The term "total energy" means the total energy under a load versus elongation curve as expressed in weight-length units. The term "elongation" means the increase in length of a specimen during a tensile test. The grab tensile test uses two clamps, each having two jaws with each jaw having a facing in contact with the sample. The clamps hold the material in the same plane, usually vertically, separated by 3 inches (76 mm) and move apart at a specified rate of extension. Values for grab tensile strength and grab elongation are obtained using a sample size of 4 inches (102 mm) by 6 inches (152 mm), with a jaw facing size of 1 inch (25 mm) by 1 inch, and a constant rate of extension of 300 mm/min. The sample is wider than the clamp jaws to give results representative of effective strength of fibers in the clamped width combined with additional strength contributed by adjacent fibers in the fabric. The specimen is clamped in, for example, a Sintech 2 tester, available from the Sintech Corporation, 1001 Sheldon Dr., Cary, N.C. 27513, an Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154. This closely simulates fabric stress conditions in actual use. Results are reported as an average of three specimens and may be performed with the specimen in the cross direction (CD) or the machine direction (MD).

Strip Tensile: The strip tensile test is similar to the grab tensile and measures the peak and breaking loads and peak and break percent elongations of a fabric. This test measures the load (strength) in grams and elongation in percent. In the strip tensile test, two clamps, each having two jaws with each jaw having a facing in contact with the sample, hold the material in the same plane, usually vertically, separated by 3 inches and move apart at a specified rate of extension. Values for strip tensile strength and strip elongation are obtained using a sample size of 3 inches by 6 inches, with a jaw facing size of 1 inch high by 3 inches wide, and a constant rate of extension of 300 mm/min. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154 may be used for this test. Results are reported as an average of three specimens and may be performed with the specimen in the cross direction (CD) or the machine direction (MD).

Peel test: In peel or delamination testing a laminate is tested for the amount of tensile force which will pull the layers of the laminate apart. Values for peel strength are obtained using a specified width of fabric, clamp jaw width and a constant rate of extension. For samples having a film side, the film side of the specimen is covered with masking tape or some other suitable material in order to prevent the film from ripping apart during the test. The masking tape is on only one side of the laminate and so does not contribute to the peel strength of the sample. This test uses two clamps, each having two jaws with each jaw having a facing in contact with the sample, to hold the material in the same plane, usually vertically, separated by 2 inches to start. The sample size is 4 inches wide by as much length as necessary to delaminate enough sample length. The jaw facing size is 1 inch high by at least 4 inches wide, and the constant rate of extension is 300 mm/min. The sample is delaminated by hand a sufficient amount to allow it to be clamped into position and the clamps move apart at the specified rate of extension to pull the laminate apart. The sample specimen is pulled apart at 180° of separation between the two layers and the peel strength reported as an average of peak load in grams. Measurement of the force is begun when 16 mm of the laminate has been pulled apart and continues until a total of 170 mm has been delaminated. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or the Thwing-Albert Model INTELLECT II available from the Thwing-Albert Instrument Co., 10960 Dutton Rd., Phila., Pa. 19154, may be used for this test. Results are reported as an average of three specimens and may be performed with the specimen in the cross direction (CD) or the machine direction (MD).

Martindale Abrasion test: This test measures the relative resistance to abrasion of a fabric. The test results are reported on a scale of 1 to 5 with 5 being the least wear and 1 the most, after 120 cycles with a weight of 1.3 pounds per square inch. The test is carried out with a Martindale Wear and Abrasion Tester such as model no. 103 or model no. 403 available from James H. Heal & Company, Ltd. of West Yorkshire, England. The abradant used is a 36 inch by 4 inch by 0.05 thick silicone rubber wheel reinforced with fiber glass having a rubber surface hardness 81A Durometer, Shore A of 81 plus or minus 9. The abradant is available from Flight Insulation Inc., a distributor for Connecticut Hard Rubber, 925 Industrial Park, NE, Marietta, Ga. 30065.

Handle-O-Meter: The softness of a nonwoven fabric may be measured according to the "Handle-O-Meter" test. The test used herein is the INDA standard test 1st 90.0-75 (R 82) with two modifications: 1) the specimen size was 4 inches by 4 inches and 2) five specimens were tested rather than two. The test was carried out on Handle-O-Meter model number 211-5 from the Thwing-Albert Instrument Co., 10960 Dutton Road, Phila. Pa. 19154. The Handle-O-Meter reading is on a scale of 1 to 5.

Hydrohead: A measure of the liquid barrier properties of a fabric is the hydrohead test. The hydrohead test determines the height of water (in mbars) which the fabric will support before a predetermined amount of liquid passes through. A fabric with a higher hydrohead reading indicates it has a greater barrier to liquid penetration than a fabric with a lower hydrohead. The hydrohead test is performed according to Federal Test Standard 191A, Method 5514.

DETAILED DESCRIPTION

Many different thermal bonding patterns have been developed for nonwoven fabrics in order to give them integrity for further processing into finished materials, for bonding to other materials (e.g. nonwovens and films) and to impart particular visual markers. Some patterns for sterile wrap applications, for example, provide indicators to help show where the fabric should be folded. Patterns for diapers and wipes can include "baby objects" such as bears, trains, etc. More utilitarian patterns have been developed for applications such as car covers and oil absorption materials.

Figure 4:
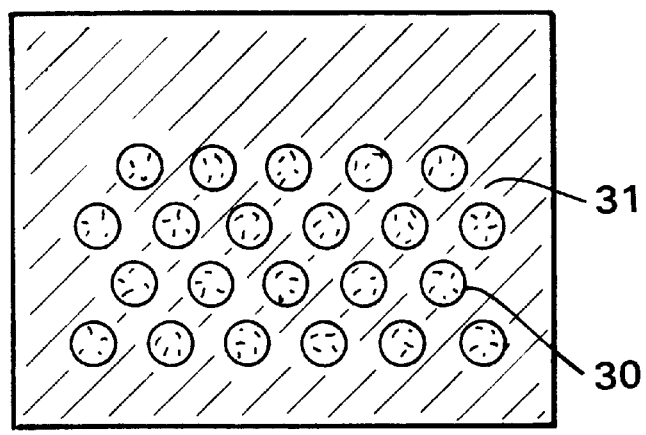
FIG. 4 is a drawing of a pattern according to U.S. patent application Ser. No. 08/754,419 known as a Point Unbonded Pattern or PUB.

One recently developed pattern is known as a point unbonded or PUB pattern and includes unbonded fabric surrounded 100 percent by bond area, an example of which is shown in FIG. 4. This pattern generally may have a bond area of from about 25 to about 50 percent. The complete surrounding of an unbonded area gives this pattern good abrasion resistance and nonwoven fabrics having this pattern have found utility as, for example, the "loop" in hook and loop fastening systems. Such fabrics may be found in the landing zone on some Huggies® diapers. The complete surrounding of an unbonded area is believed to significantly reduce fiber mobility by tying down all loose ends within a small area. While useful for many applications requiring toughness, fabrics with this pattern can be somewhat stiff.

Figure 2:
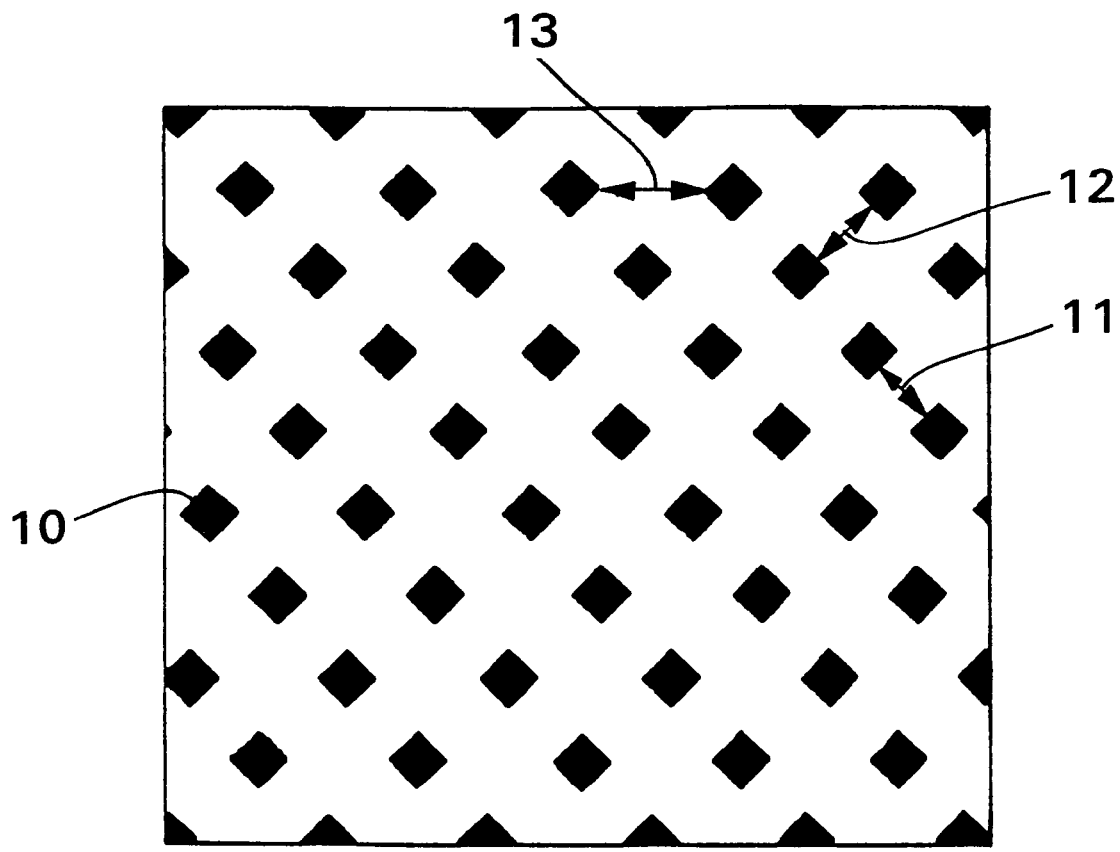
FIG. 2 is a drawing of a bonding pattern according to U.S. Pat. No. 3,855,046 known as an Expanded Hansen-Pennings or EHP pattern.

An older pattern is that known as an Expanded Hansen-Pennings or "EHP" bond pattern. The EHP patterns has a bond area generally from about 10 to about 30 percent, an example of which is shown in FIG. 2. Higher bond areas are possible but usually result in stiff fabrics unsuitable for many applications. The EHP pattern does not completely surround an unbonded area and so fiber mobility and softness are greater than in a PUB fabric, however abrasion resistance and strength are lower than a PUB fabric at the same bond area.

In order to avoid the trade-off between abrasion resistance and softness seen in the PUB, EHP and other patterns, the inventors have developed a pattern wherein an unbonded area is not completely surrounded by bond area but is surrounded to a large degree. This pattern provides sufficient numbers of immobilized fibers to strengthen the fabric, yet not so much as to increase stiffness unacceptably.

Testing of fabrics bonded with an example of the inventive pattern (called by the inventors "S-weave") and with EHP bonded fabrics showed a surprising increase in abrasion resistance and hydrohead with good strength and acceptable softness. Details of the fabrics and the testing follow.

EXAMPLE 1

A laminate was produced using a nonwoven layer and a film layer.

The nonwoven layer was a 20 gsm layer of fabric made by a spunbond process with 2 denier fibers produced from a polypropylene copolymer having about 3.5 weight percent ethylene. The copolymer was produced by the Union Carbide Company under the designation 6D43. The nonwoven fabric so produced was thermally self bonded with either the EHP pattern of FIG. 2 or the S-weave pattern of FIG. 1.

The film was a multilayer film having a bonding layer and an outer layer. The film was produced by coextrusion and had an overall basis weight was 58 gsm. The bonding layer was made from about 55 weight percent Supercoat™ $CaCO_3$ (available from English China Clay of Sylacauga, Ala., and having a coating of about 1.5 weight percent of either stearic or behenic acid to enhance dispersion of the filler), 45 weight percent Dow AFFINITY® EG 8200 low density elastomeric metallocene catalyzed polyethylene having a density of $0.87 g/cm^3$ and a melt index at 190° C. of 5 g/10 min. The outer layer was made of about 50 weight percent Supercoat™ $CaCO_3$, 45 weight percent DOWLEX® NG 3310 linear low density polyethylene having a density of about 0.918 g/cm3 and a melt index at 190° C. of 3.5 g/10 min., 5 weight percent Dow low density polyethylene 4012, and about 2000 ppm of Ciba Geigy's B900 stabilizer.

The co-extruded film was stretched in the machine direction in a single stretching operation to about 391 percent of its original length. Prior to stretching, the film was preheated by passing it around a series of rolls at about 49° C. In the stretching step, the film was held back by a slow roll at about 66° C. and drawn by a fast roll at about 21° C. The stretched film was then annealed by passing over another roll without stretching at about 82° C.

The stretched film and pre-bonded nonwoven were fed to a thermal point bonder and laminated together using a heated pattern roll at about 93° C. and a smooth steel anvil roll at about 88° C. with a nip pressure of about 175 pounds per linear inch. The pattern roll used a baby objects pattern which imparts about a 15 percent bond area to the laminate.

The resulting laminate made with the nonwoven fabric and film had a basis weight of about 42 gsm. The laminate with the fabric having an S-weave pattern had an unsupported hydrohead of about 95 mbar when 1 drop of water of water emerged on the opposite side and an MD peel strength of 226 gms. The laminate with the fabric having an EHP pattern had an unsupported hydrohead of about 61 mbar when 1 drop of water emerged on the opposite side and an MD peel strength of about 298 gms. Note that these results are averages for three separate measurements.

EXAMPLE 2

Samples of the nonwoven fabric (only) from Example 1 were tested for Martindale abrasion, Handle-o-meter, tensile strength, and grab tensile. The results are given in Table 1.

TABLE 1

|  | Bond Area % | Basis Weight osy | Strip Tensile MD grams | Strip Tensile CD grams | Handle-O-Meter MD | Handle-O-Meter CD | grab MD pk gm | grab CD pk gm | Martindale Abrasion scale 1–5 |
|---|---|---|---|---|---|---|---|---|---|
| S-weave | 17.7 | 0.65 | 6717 | 3549 | 7 | 2.5 | 5061 | 3589 | 5 |
| EHP | 16.8 | 0.697 | 4373 | 2004 | 6.7 | 1.3 | 3867 | 2188 | 3 |

Comparative Example 1

As a comparative example, samples of nonwoven fabric (only) made from the same polymer as in the above Examples and having a rib-knit (RK) pattern according to U.S. Pat. No. 5,620,779 and wire weave (WW) pattern were tested in the same manner as in Example 2. This information is shown below in Table 2.

TABLE 2

|  | Bond Area % | Basis Weight osy | Strip Tensile MD grams | Strip Tensile CD grams | Handle-O-Meter MD | Handle-O-Meter CD | grab MD pk gm | grab CD pk gm | Martindale Abrasion scale 1–5 |
|---|---|---|---|---|---|---|---|---|---|
| RK | 16.5 | 0.56 | 3551 | 3168 | 3.8 | 2 | 3988 | 3288 | 3 |
| WW | 18 | 0.59 | 4187 | 3234 | 7 | 3.3 | 2826 | 3366 | 4.4 |

The results from the S-weave examples show an increase in strength and abrasion resistance while maintaining acceptable softness. Hydrohead in a laminate form with film also was increased. These increases are quite surprising since both the S-weave and EHP patterns have about the same bond area, bond density and basis weight.

In alternative embodiments an S-weave patterned fabric or laminate may be stretched in order to create perforations or apertures in the material according to, for example, the neck stretching patents cited above or U.S. Pat. No. 4,588,630 to Shimalla, U.S. Pat. No. 3,949,127 to Ostermeier et al. and U.S. Pat. No. 5,628,097 to Benson et al. which involve stretching a fabric after patterning in order to open the fabric at the bond points.

The S-weave type of pattern is best understood by examining the aspect ratio of the elements or pins of the pattern as well as the unbonded fiber aspect ratio.

Figure 3:
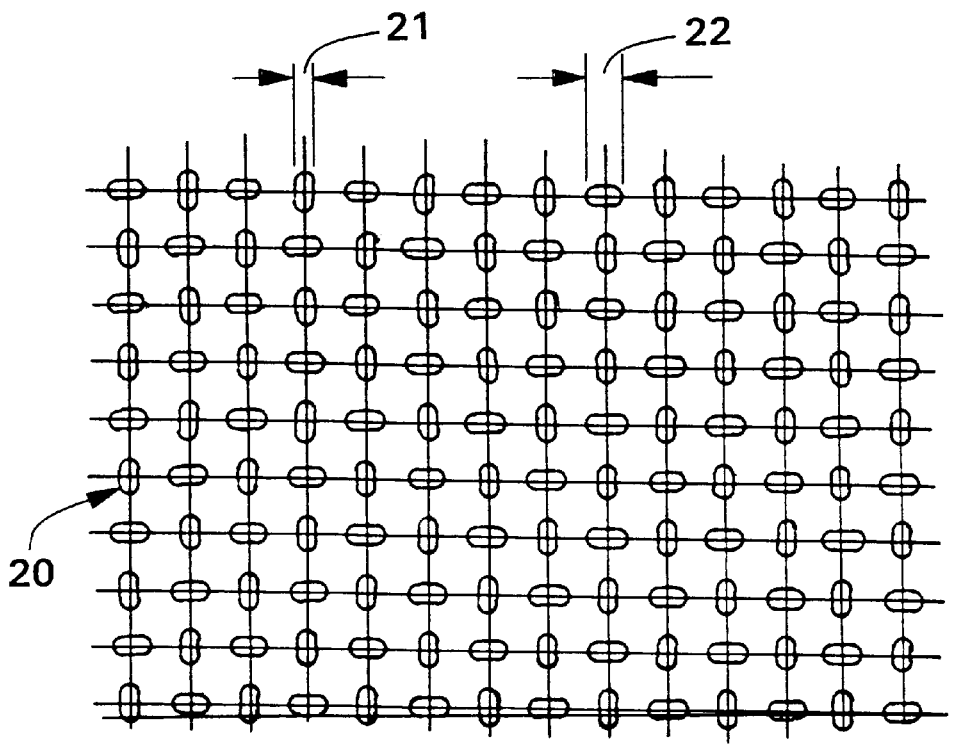
FIG. 3 is a drawing of a bonding pattern known in the art as a wire weave pattern.

Turning now to the drawings, note that the lines drawn on FIGS. 2 and 3 are for illustrative purposes only and do not form part of the patterns. The elements or pins only form the patterns.

FIG. 1 is an example of a pattern fitting the requirements of the invention. FIG. 1 has elements or pins 1 which are identical. The pins have a center to center spacing 2 of 0.143 inches and a minimum spacing 3 of 0.0288 inches. The pins are 0.012 inches wide and 0.1226 inches long along the centerline.

FIG. 2 has a pattern of square tapered points 10 with a wide spacing 11 of 0.0664 inches and a narrow spacing 12 of 0.0526 inches. The pins are all 0.037 inches across.

FIG. 3 has identical elongated oval shaped elements 20 which have a width of 21 of 0.016 inches and length 22 of 0.031 inches.

FIG. 4 has fibers 30 completely surrounded by bond area 31 which is shown diagonally lined.

The element aspect ratio for the EHP pattern shown in FIG. 2 is 1 since the length and width of the element are the same, i.e., the bonds are square. The wire weave pattern of FIG. 3 has elements of length 0.031 inches and width of 0.016 inches for an element aspect ratio (0.031/0.016) of about 2. The element aspect ratio for the S-weave pattern shown in FIG. 1, for example, is 0.1226/0.012 inches or about 10. Ratios as high as 20 and as low as 2 are believed to work wherein ratios beyond these limits will suffer from stiffness (more than 20) or lack of integrity (less than 2). More particularly a ratio of between about 7 and 15 is desirable or still more particularly, between about 8 and 12.

Also required is that the unbonded areas of the pattern be sufficiently large. This ensures that enough fibers will be free for use, for example, as a loop material for a hook and loop fastening system. This also helps ensure that the fiber will not be too stiff. In the case of FIG. 2, the unbonded fiber aspect ratio is about 3 and in the case of FIG. 3 about 1.7. The S-weave pattern of FIG. 1 has an unbonded fiber aspect ratio of about 5 as calculated by 0.143/0.0288. Ratios as high as 10 and as low as 3 are believed to work, more particularly a ratio of between about 8 and 3 is desirable or still more particularly, between about 6 and 4.

The bond area is also important in describing the bond pattern of this invention since a highly bonded pattern would be entirely too stiff. The inventors have found that a bond area percentage of less than about 30 percent is required, more particularly between about 10 and 25 percent and still more particularly between about 15 and 20 percent.

Another aspect of the S-weave pattern is the pin density of the pattern. Some bonding patterns may have pin densities of as much as 500 pins per square inch, while the S-weave and EHP patterns are generally in the 50–200 pin/in$^2$ range, more preferably about 75–150, and, in the Examples, about 100. The patterns of U.S. Pat. No. 5,620,779, for example, have pin densities in the 200–300 range, and the well known wire weave pattern usually has a pin density of about 300, even when bonded with approximately the same bond area as an S-weave or EHP pattern. The RK pattern and WW patterns of the Comparative Example had pin densities of about 242 and 302, respectively. Its believed that higher pin densities with about the same bond area tie down more fibers, i.e., reduce fiber freeness, and so serve to stiffen a fabric and reduce softness.

The novel S-weave pattern may be used to self-bond fabrics and should be distinguished from patterns made to laminate materials together which are significantly different. The S-weave pattern may be used with any thermally bondable fiber, monocomponent, biconstituent, conjugate, coform etc.

The pattern of FIG. 1, for example, satisfies the requirements of the invention and produces a fabric with abrasion resistance and strength greater than a fabric bonded with a like amount of bond area but without the required aspect ratios. The hydrohead for nonwoven/film embodiments is also superior to fabrics having similar bond area but aspect ratios outside of the invention requirements.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

It should be noted that this patent application is one of a series of applications being filed on the same date, having the same assignee, and incorporated herein by reference in their entirety. In addition to the instant applications, these are:

"Stretch-pillowed Bulked Laminate Useful as an Ideal Loop Fastener Component", inventors: McCormack and Haffner, Attorney docket no. 13520.

"Breathable Barrier Composite Useful as an Ideal Loop Fastener Component", inventors: McCormack, Haffner and Jackson, Attorney docket no. 13148.

What is claimed is:

1. A pattern bonded nonwoven fabric comprising a nonwoven fabric having a pattern of bonds providing a bond area, said pattern having an element aspect ratio between about 2 and about 20 and an unbonded fiber aspect ratio of between about 3 and about 10.

2. The nonwoven fabric of claim 1 which has a bond area between about 5 and about 30 percent.

3. The nonwoven fabric of claim 1 which has a bond density between about 50 and about 200 pins per square inch.

4. The nonwoven fabric of claim 1 which has been thermally bonded.

5. The nonwoven fabric of claim 4 having an abrasion resistance and strength greater than a fabric having a similar bond area but an element aspect ratio less than 2.

6. The nonwoven fabric of claim 4 having an abrasion resistance and strength greater than a fabric having a similar bond area but having an unbonded fiber aspect ratio less than 3.

7. The fabric of claim 4 which is stretched to produce perforations.

8. A diaper comprising the fabric of claim 4.

9. A wiper comprising the fabric of claim 3.

10. An incontinence product comprising the fabric of claim 4.

11. A feminine hygiene product comprising the fabric of claim 4.

12. An infection control product comprising the fabric of claim 4.

13. A laminate comprising a nonwoven fabric having the pattern of claim 1 and a film, thermally bonded together.

14. The laminate of claim 13 which is stretched to produce perforations.

15. A thermally bonded nonwoven fabric comprising nonwoven fabric having a pattern of bonds and having a bond area, said pattern having an element aspect ratio between about 7 and about 15 and an unbonded fiber aspect ratio of between about 8 and about 3.

16. The thermally bonded nonwoven fabric of claim 15 having a bond area of less than about 30 percent.

17. The thermally bonded nonwoven fabric of claim 15 wherein said element aspect ratio is between 8 and 12.

18. A thermally bonded nonwoven fabric comprising nonwoven fabric having a pattern of bonds and having a bond area, said pattern having an element aspect ratio between about 8 and about 12, said bond area being between about 15 and 20 percent, and an unbonded fiber aspect ratio between about 6 and about 4.

19. A laminate comprising a film and the nonwoven fabric of claim 18.

20. The laminate of claim 19 further comprising apertures at said bonds produced by stretching said laminate.

21. The fabric of claim 18 wherein said pattern has a bond density between about 75 and about 150 pins per square inch.

* * * * *